United States Patent [19]

Sattler et al.

[11] 4,325,635
[45] Apr. 20, 1982

[54] HETERODYNE INDICIAL REFRACTOMETER

[75] Inventors: Joseph P. Sattler; Terrance L. Worchesky, both of Silver Spring; Kenneth J. Ritter, Adelphi, all of Md.

[73] Assignee: The United States of America as represented by the Secretary of the Army, Washington, D.C.

[21] Appl. No.: 194,736

[22] Filed: Oct. 7, 1980

[51] Int. Cl.³ .............................................. G01B 9/02
[52] U.S. Cl. .................................... 356/349; 356/361
[58] Field of Search ....................... 356/346, 349, 361

[56] References Cited

PUBLICATIONS

Tanaka et al. "Laser Heterodyne Measurements of Photo-Inducal Refractive-Index Changes in Amorphous As–S Films", *Optics Communications*, vol. 19, No. 1, pp. 134–137, 10/76.

Lavan, "Optical Heterodyne Interferometer with Radio Frequency Phase Reference", *Applied Optics*, vol. 15, pp. 2627–2628, 11/76.

*Primary Examiner*—John K. Corbin
*Assistant Examiner*—Matthew W. Koren
*Attorney, Agent, or Firm*—Nathan Edelberg; Robert P. Gibson; Saul Elbaum

[57] ABSTRACT

A method and apparatus for simply and accurately determining the index of refraction of semiconductor materials, etalon bars and materials transparent to infrared radiation. The channel spectra of the material is obtained by passing through it a portion of radiation from a continuously tuned diode laser. Another portion of the diode laser radiation is heterodyned with radiation from a $CO_2$ laser to obtain heterodyne marker beats. The channel spectra and marker beats are displayed in conjunction whereby the frequency difference between the marker beats can be related to the number of fringes in the channel spectra between the marker beats.

12 Claims, 4 Drawing Figures

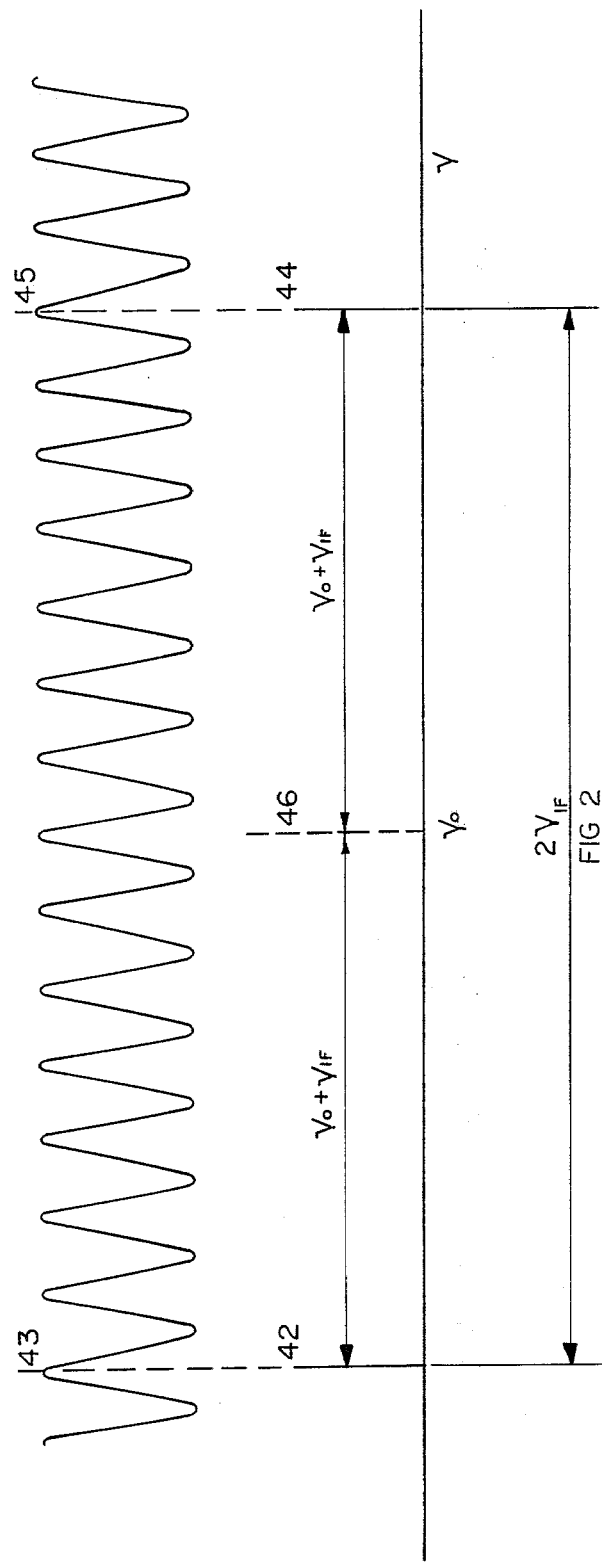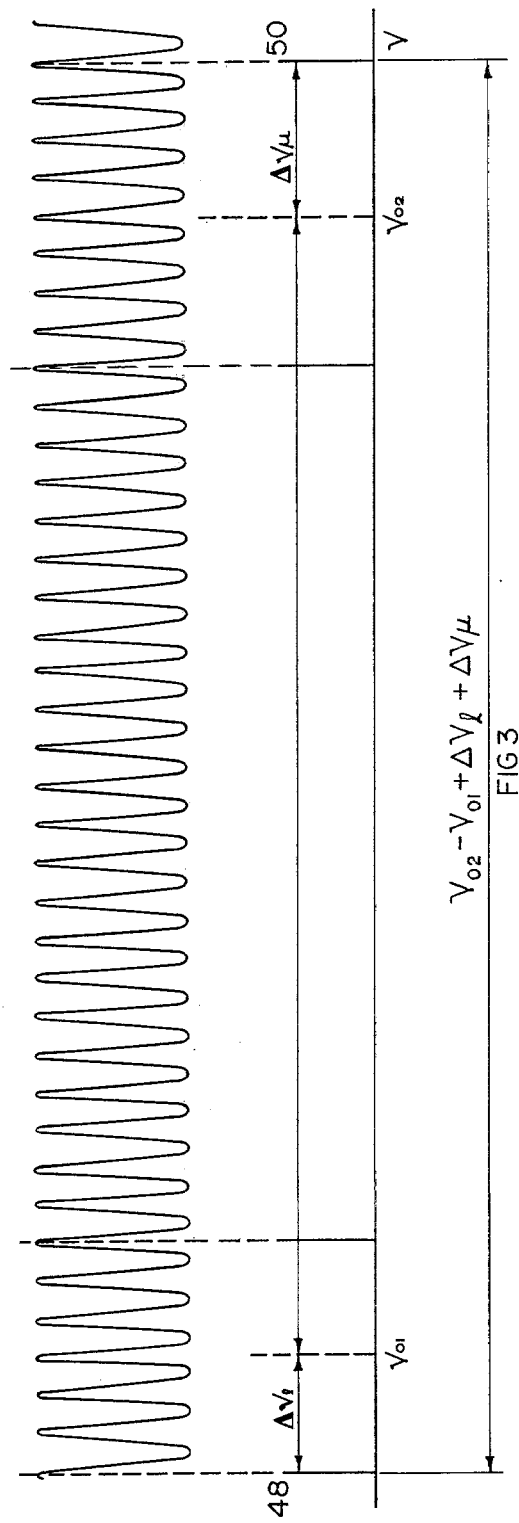

HETERODYNE INDICIAL REFRACTOMETER

RIGHTS OF THE GOVERNMENT

The invention described herein may be manufactured, used or licensed by or for the government of the United States of America for governmental purposes without payment to us of any royalties therefor.

BACKGROUND OF THE INVENTION

This invention relates generally to diode-laser spectrometers and more particularly to a tunable diode-laser heterodyne spectrometer that is modified to provide an apparatus and method to determine the index of refraction of materials such as semiconductor materials and etalon bars. The index of refraction of semiconductor materials such as Ge, Si, HgCdTe, InSb, GaAs and any other material transparent to tunable infrared laser radiation can be accurately determined.

Materials in the form of etalon bars have been used for years for calibrating frequency, in interferometers as standards of length and in conjunction with diode lasers to give alternate transmission and reflection peaks. However, there is no method to accurately determine the index of refraction of these materials. Because of the different doping concentrations used in semiconductor materials there is a need to be able to determine the optical properties simply and accurately for each of these materials.

It is therefore one object of this invention to provide a method of determining the index of refraction of semiconductor materials.

It is another object of this invention to provide a method of determining the index of refraction that is simple and accurate.

It is a further object of this invention to provide a method of determining the index of refraction of materials that are transparent to tunable infrared laser radiation.

It is still another object of this invention to provide an apparatus that can determine the index of refraction of semiconductor materials rapidly, simply and accurately.

It is still a further object of this invention to provide an apparatus that can determine the index of refraction of materials that are transparent to tunable infrared laser radiation.

Other objects, advantages and novel features of the present invention will become apparent from the following detailed description of the invention when considered in conjunction with the accompanying drawings.

SUMMARY OF THE INVENTION

These and other objects, features and advantages of the invention are accomplished by an apparatus and method wherein the channel spectra of the material is determined by directing a portion of continuously tuned diode-laser radiation through the material. Another portion of the diode-laser radiation is heterodyned with radiation from a fixed frequency laser to produce heterodyne beats. Heterodyne marker beats are selected and displayed in conjunction with the channel spectra whereby the number of fringes between the marker beats can be related to the frequency difference between the marker beats.

BRIEF DESCRIPTION OF THE DRAWINGS

The above and further objects and novel features of the invention will more fully appear from the following description when the same is read in connection with the accompanying drawings. It is to be understood, however, that the drawings are for the purpose of illustration only, and are not intended as a definition of the limits of the invention.

FIG. 2 is a graphical representation of the displayed channel spectra and the heterodyned marker beats using a single fixed frequency.

FIG. 3 is a graphical representation of the displayed channel spectra and the heterodyned marker beats using multiple fixed frequencies.

FIG. 4 is a graphical representation of an actual display of the channel spectra of a 3 inch etalon bar and the heterodyned marker beats using the 10R34 and 10R36 lines from a $CO_2$ laser.

DESCRIPTION OF THE PREFERRED EMBODIMENT

Figure 1:
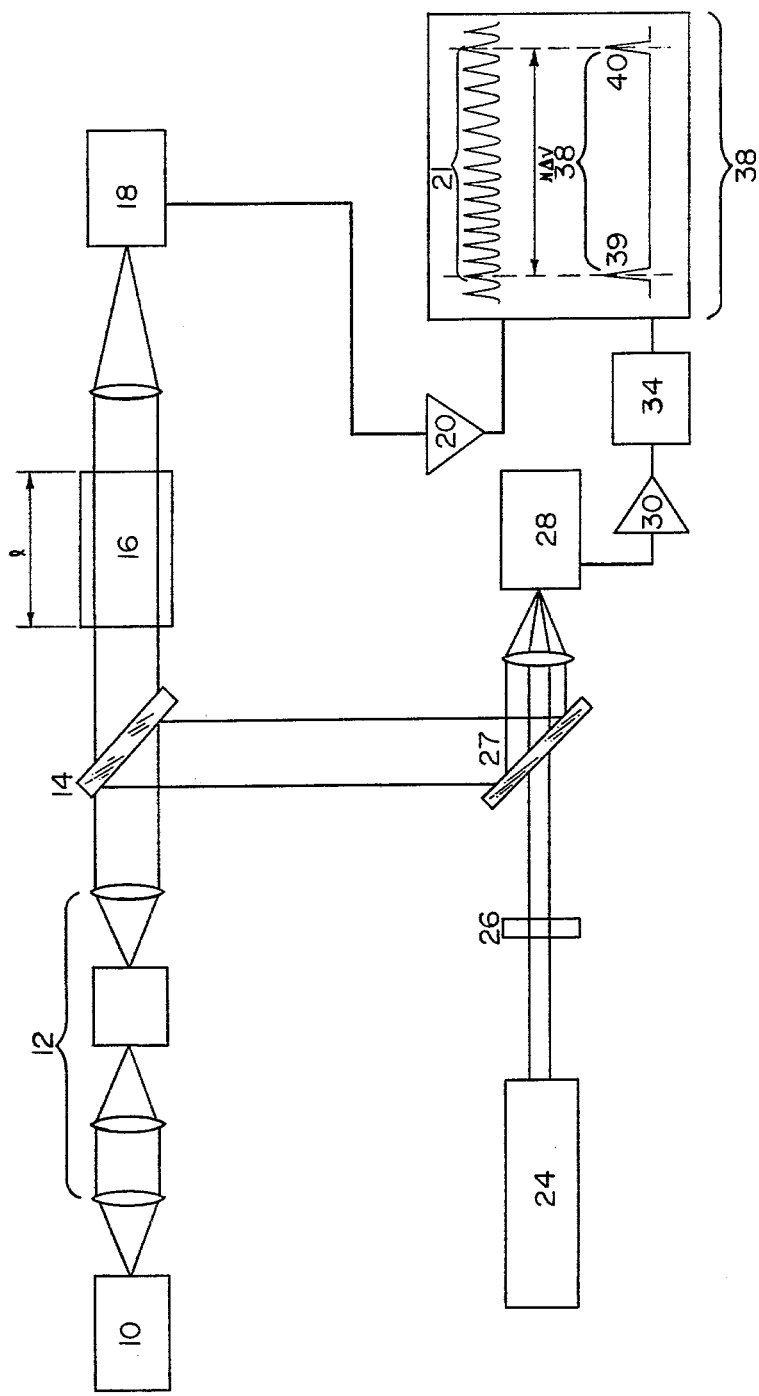
FIG. 1 illustrates schematically the method and apparatus of the present invention.

Referring now to the drawings, FIG. 1 is a schematic representation of an apparatus illustrating the method to measure the index of refraction of a material. A first source of radiation 10 such as a Pb-salt-diode laser provides continuously tunable radiation. The diode laser 10 is mounted in a closed-cycle cryogenic refrigerator. The output frequency of the diode laser 10 is coarsely tuned by varying the cold-sink temperature. The diode laser 10 is fine-tuned by adjusting the average value and amplitude of the injection current, which can be done, for example, by inputing the injection current in the form of a sawtooth ramp. Because the output of a diode laser is in several modes of different frequency, the lens and monochrometer system, shown generally at 12, is used to eliminate all but one mode. The output beam of radiation after passing through the monochrometer is divided into portions by a beam splitter 14. One portion of the beam is passed through a bar 16 of the material whose index of refraction is to be determined. The length l of the material is accurately premeasured. As is known, the varying frequency of radiation passing through the bar 16 produces transmission and reflection peaks known as a channel spectrum. The channel spectrum is detected by a detector 18 and coverted to an electrical signal which is amplified by an amplifier 20 and displayed by a video display unit 38. One example of an appropriate detector 18 is an HgCdTe detector operating in a video detection mode.

Another portion of the diode laser beam split by beam splitter 14 is directed to a photomixer 28 by a beam splitter 27. The photomixer 28 mixes the radiation from the diode laser 10 with radiation from a well determined fixed frequency source 24 to produce heterodyne beats. An example of a fixed frequency source 24 is a local-oscillator $CO_2$ laser with an intracavity diffraction grating for line selection and a piezoelectric transducer for setting the laser to line center by optimizing the output power. Attenuator 26 is used to attenuate the output of the $CO_2$ laser to better match the output power of the diode laser. Photomixer 28 can be any appropriate type known in the art such as an SAT Model C4HgCdTe photomixer with a 3-dB bandwidth of 1.2 GHz. The signals from the photomixer 28 are amplified by a low-noise (N.F.≃4.5 dB) wideband amplifier 30 and are input to a spectrum analyzer 34. The spectrum analyzer 34 is operated as a tunable narrow-band (100 or 300 kHz) receiver and is tuned to a selected $\nu_{IF}$ to receive only those heterodyne marker beats that occur when the frequency difference between the two input beams of radiation is equal to the selected frequency, $\nu_{IF}$. For example, if the frequency of the second source of radiation is $\nu_o$ then the spectrum analyzer will receive only those marker beats that occur when the frequency of the first source of radiation is $\nu_o - \nu_{IF}$ (herein termed the lower marker beat) or $\nu_o + \nu_{IF}$ (herein termed the upper marker beat). The lower marker beat 39 and the upper marker beat 40 are displayed by display unit 38 in conjunction with the channel spectra 21.

The relationship between the channel spectra and the marker beats will be explained in conjunction with FIGS. 2-4. FIGS. 2 and 3 are graphical representations of the video display of channel spectra and the heterodyned marker beats. FIG. 4 is a display of the channel spectra of a three inch germanium etalon bar and the marker beats heterodyned using a diode-laser and the 10R34 and 10R36 frequencies of the $CO_2$ laser.

Referring now to FIG. 2 the upper curve represents the channel spectra that is obtained by directing a beam of continuously tuned radiation through a bar of material transparent to the radiation. The channel spectra is displayed electronically as a sinusoidal type curve with alternating maxima and minima. One maxima and one minima is known optically as a fringe. The condition for maximum transmission of monochromatic light through an etalon bar is that an integral number of wavelengths fit into twice the optical path ($n \times l$) where n is the index of refraction and l is the bar's length. Thus, for example, at the position of maximum transmission 45, FIG. 2, $N_2 \lambda_2 = 2n_2 l$ and at position 43, FIG. 2, $N_1 \lambda_1 = 2n_1 l$ where $N_2$ is the number of wavelengths of wavelength $\lambda_2$ and $N_1$ is the number of wavelength $\lambda_1$. Using the relationship $\lambda \nu = c$, where $\lambda$ is the wavelength, $\nu$ is the frequency and c is the speed of light we obtain $$N_2 = 2n_2 l \frac{\nu_2}{c}$$

and $$N_1 = 2n_1 l \frac{\nu_1}{c}$$

Thus, $$N_2 - N_1 = \Delta N = \frac{2l}{c}(n_2\nu_2 - n_1\nu_1)$$

Expanding, $$n_1 = n_2 - \frac{\partial n}{\partial \nu} \Delta \nu$$

then $$\Delta N = \frac{2l}{c}(\nu_2 - \nu_1)n' = \frac{2l}{c} \Delta \nu n'$$

where $$n' = n_2 + \nu_1 \frac{\partial n}{\partial \nu}$$

where n' is the effective index of refraction of the etalon bar. The true index, $n_2$, may be determined from n' by using tabulated values of $\partial n/\partial \nu$. The method of precisely determining n' is the subject of the present invention. The present invention describes a method and apparatus to accurately measure $\Delta N$, $\nu_2$ and $\nu_1$. The length of the etalon bar is determined by techniques well known in the art. As can be appreciated by those or ordinary skill in the art the temperature effects must be accounted for. Thus, when the length l of the etalon bar is measured it should be measured at the same temperature at which $\Delta N$, $\nu_2$ and $\nu_1$ are measured. As can also be appreciated, to eliminate thermal changes in l and n it is necessary to keep the etalon bar in a constant temperature environment during the measurement, so that the difference in temperature is less $1 \times 10^{-3}$ degrees Kelvin.

The true index at $\nu_2$ is $n_2$ and this may be accurately calculated from the measured values of n', $\nu_1$ and the tabulated values of $\partial n/\partial \nu$. For example, $\partial n/\partial \nu$ need only to be known to one part in one hundred to allow n to be calculated to better than one part in ten thousand. Since the values of $\partial n/\partial \nu$ are tabulated to better than one part in one hundred it can be appreciated the accuracy of the method and apparatus of the present invention.

To determine the effective index of refraction n' the number of fringes $\Delta N$ and the frequency spacing $\Delta \nu$ is determined as follows. The spectrum analyzer 34, FIG. 1, is tuned to receive a frequency $\nu_{IF}$. Marker beats 42, 44 will be displayed whenever the frequency difference between the frequency $\nu_o$ of the fixed frequency source 24 and the tunable frequency source 10 is equal to $\nu_o \pm \nu_{IF}$. Thus, lower marker beat 42 is displayed when the heterodyne frequency is $\nu_o - \nu_{IF}$ and upper marker beat 44 is displayed when the heterodyne frequency is $\nu_o + \nu_{IF}$. The fixed frequency $\nu_o$ is not displayed but for illustrative purposes is shown as a dashed line 46. Therefore, it is apparent that $\Delta \nu$ is then equal to $(\nu_o + \nu_{IF}) - (\nu_o - \nu_{IF})$ which is equal to $2\nu_{IF}$. Therefore, $2\Delta \nu_{IF} = \Delta Nc/2n'l$ and it follows that $n' = \Delta Nc/4\nu_{IF}l$. By visually displaying the channel spectra the number of fringes $\Delta N$ can be determined and the quantity, $\nu_{IF}$, is taken from the spectrum analyzer 34. With these two values and the premeasured length, l, the index of refraction n' can be determined. However, FIG. 2 represents an ideal situation with the marker beats 42 and 44 coinciding exactly with maxima points 43 and 45 respectively. With the frequency $\nu_{IF}$ of the spectrum analyzer 34 set at a particular frequency to align one of the marker beats with a maxima the other marker beat will usually not be aligned with a maxima. This presents the problem of determining fractions of fringes which introduces an error into the calculation. This is solved by displaying the channel spectra and marker beats on a display unit such as a dual trace oscilloscope, injecting the diode laser 10 with a ramp current input, such as an 80 Hz ramp current and triggering the oscilloscope with the onset of the ramp current. Thus a repeatable display is obtained and the lower marker 42 can be aligned with a maxima 43 very accurately by tuning the spectrum analyzer 34 to a frequency $\nu_{IF1}$. The upper marker 44 is similarly accurately aligned with a maxima 45 by tuning the spectrum analyzer 34 to a frequency $\nu_{IF2}$. Thus the number of fringes N is an integral number and n' is calculated from the relationship $n' = \Delta Nc/2(\nu_{IF1} + \nu_{IF2})l$.

FIG. 3 is another alternative method by which the measurement error can be further reduced. The measurement error can be reduced by spreading the error over a larger number of fringes $\Delta N$. However, the number of fringes $\Delta N$ obtainable in the method described above is limited by the characteristics of the photomixer 28 and the maximum frequency $\nu_{IF}$ presently obtainable is approximately 8.5 GHz. Therefore, the number of fringes $\Delta N$ obtainable is limited to the number of fringes in the channel spectra in a frequency difference of about 17 GHz. By using a laser with a multimode output such as a $CO_2$ laser the number of fringes between the marker beats can be expanded. This is done, as shown in FIG. 3 by using a lower marker beat 48 heterodyned from one frequency mode $\nu_{o1}$ of the $CO_2$ laser and an upper marker beat 50 heterodyned from a higher frequency mode $\nu_{o2}$ of the $CO_2$ laser. As discussed above, the frequencies at which the lower and upper markers 48, 50 occur are adjusted until the marker beats coincide with a maxima of the channel spectra. In FIG. 4, the two frequency modes of the $CO_2$ laser were the 10R34 and 10R36 frequency modes. The heterodyne frequency was set, on the spectrum analyzer 34, at 4.5 GHz. The relationship between the index of refraction, the number of fringes and the frequency difference is then $$n' = \Delta Nc/2\{(\nu_{o2} - \nu_{o1}) + (\Delta \nu_u + \Delta \nu_l)\}l$$

$$n' = 87c/2\{(\nu_{o2} - \nu_{o1}) + 2(4.5 \text{ GHz})\}l$$

where
$\Delta N = 87$ (counted from FIG. 3)
$\Delta \nu_u = \Delta \nu_l = 4.5$ GHz
$\nu_{o2} = \nu(10R36$ of $CO_2$ laser$)$
$\nu_{o1} = \nu(10R34$ of $CO_2$ laser$)$
$l =$ known length of etalon bar While we have described and illustrated several specific embodiments of our invention, it will be clear that variations of the method and apparatus which are specifically illustrated and described may be resorted to without departing from the true spirit and scope of the invention as defined in the appended claims.

What we claim is:

1. A method of measuring the index of refraction of a material which comprises the steps of:
    obtaining a first beam of radiation by continuously tuning a first source of radiation through a selected range of frequencies;
    determining the channel spectra of the material by directing a portion of the first beam of radiation through a known length of the material;
    obtaining heterodyne marker beats by heterodyning a portion of the first beam of radiation with a second beam of radiation from a second source of radiation; and
    determining the index of refraction by comparing the channel spectra to the heterodyne marker beats.

2. A method of measuring the index of refraction of a material as recited in claim 1 wherein the step of obtaining heterodyne marker beats is accomplished by:
    mixing a portion of the first beam of radiation with the second beam of radiation;
    selecting upper and lower heterodyne beats to be used as the marker beats; and
    detecting and displaying the selected marker beats.

3. A method of measuring the index of refraction of a material as recited in claim 2, wherein the step of determining the channel spectra of the material is accomplished by:
    detecting the channel spectra signal; and
    displaying the channel spectra signal in conjunction with the selected marker beats.

4. A method of measuring the index of refraction of a material as recited in claim 3, wherein the step of determining the index of refraction is accomplished by:
    determining the number of fringes in the channel spectra signal between the marker beats; and
    relating the number of fringes to the frequency difference between the marker beats.

5. A method of measuring the index of refraction of a material as recited in claim 4, wherein the first beam of radiation is obtained by injecting a current of varying amplitude into a diode laser.

6. A method of measuring the index of refraction of a material as recited in claim 5, wherein the second beam of radiation is obtained from a fixed frequency laser.

7. An apparatus to measure the index of refraction of a material comprising:
    means, continuously tunable through a selected range of frequencies, for obtaining a first beam of radiation;
    means for dividing said first beam of radiation into portions and for directing one portion of said first beam of radiation through a known length of the material;
    means for determining the channel spectra of the material;
    means for obtaining a second beam of radiation;
    means for producing heterodyne marker beats; and
    comparing means for comparing said channel spectra with said heterodyne marker beats.

8. An apparatus to measure the index of refraction of a material as recited in claim 7 wherein the means for producing heterodyne marker beats comprises:
    a photomixer, wherein a second portion of said first beam of radiation is mixed with said second beam of radiation; and
    a selection means for selecting the locations of upper and lower marker beats; and
    a means for detecting said marker beats.

9. An apparatus to measure the index of refraction of a material as recited in claim 8 wherein the means for determining the channel spectra of the material comprises a detector to detect the channel spectra signal.

10. An apparatus to measure the index of refraction of a material as recited in claim 9 wherein the comparing means comprises a visual display of said channel spectra signal and said marker beats wherein the number of fringes in said channel spectra signal is related to the frequency difference between said marker beats.

11. An apparatus to measure the index of refraction of a material as recited in claim 10 wherein the means for obtaining a first beam of radiation comprises a diode laser.

12. An apparatus to measure the index of refraction of a material is recited in claim 11 wherein the means for obtaining a second beam of radiation comprises a fixed frequency laser.

* * * * *